United States Patent [19]

Kervennal et al.

[11] Patent Number: 4,574,059
[45] Date of Patent: Mar. 4, 1986

[54] DECANE-1,10-DIISOCYANATES AND METHODS OF MAKING THE SAME

[75] Inventors: Jacques Kervennal, Lyons; Pierre Durual, Vernaison, both of France

[73] Assignee: ATOCHEM, France

[21] Appl. No.: 706,319

[22] Filed: Feb. 27, 1985

[30] Foreign Application Priority Data

Mar. 2, 1984 [FR] France .................. 84 03253

[51] Int. Cl.$^4$ .............. C07C 119/045; C07C 119/042
[52] U.S. Cl. .................. 560/347; 560/355; 564/487
[58] Field of Search ............. 260/453 AL, 453 PH, 260/453 A; 564/487

[56] References Cited

U.S. PATENT DOCUMENTS 2,865,940 12/1958 Nobis et al. .............. 260/453 AL
4,100,111  7/1978 Peter et al. .............. 564/487

Primary Examiner—Dolph H. Torrence
Attorney, Agent, or Firm—Sigalos & Levine

[57] ABSTRACT

Decane-1,10-diisocyanates corresponding to the formula

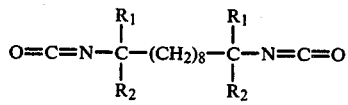

wherein $R_1$ is an alkyl or cycloalkyl radical, and $R_2$ is a hydrogen atom or an alkyl or cycloalkyl radical and the method of making these diisocyanates by the phosgenation of 1,10-diaminodecanes of the formula

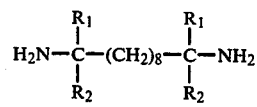

9 Claims, No Drawings

DECANE-1,10-DIISOCYANATES AND METHODS OF MAKING THE SAME

BACKGROUND OF THE INVENTION

The invention concerns aliphatic diisocyanates; particularly decane-1,10-diisocyanates, with the alkyl chain capable of being diversely substituted in positions 1 and 10. These isocyanates are prepared by the phosgenation of the corresponding amines and are especially advantageous in the synthesis of polyurethanes used particularly in the preparation of non-yellowing varnishes and paint.

Two phosgenation techniques can be advantageously implemented in order to prepare such diisocyanates. One consists of causing the amine to react at low temperature with the phosgene in a solvent in order to form carbamoyl chloride, and then to raise the temperature in order to decompose the latter and recover the isocyanate. The other one consists of synthesizing the amine chlorhydrate, isolating it, and making it react in a temperature range of 120° to 190° C., with a current of gaseous phosgene.

SUMMARY OF THE INVENTION

The diisocyanates of this invention correspond to the general formula:

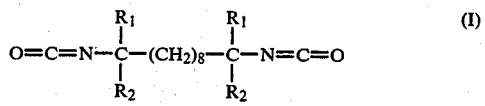

in which $R_1$ is an alkyl or cycloalkyl radical; and $R_2$ is a hydrogen atom, an alkyl or cycloalkyl radical.

The alkyl groups are radicals with a straight or branched chain preferably having from 1 to 10 carbon atoms; if they are branched, the substituents are preferably alkyl groups such a methyl, ethyl, n-propyl, isopropyl, n-, iso and tert. butyl, n-pentyl, n-hexyl, n-heptyl, n-octyl, n-decyl radicals and the like. The cycloalkyl radicals preferably contain from five to 10 carbon atoms; such as the cyclopentyl, cyclohexyl, methylcyclohexyl, cyclooctyl and the like radicals.

The invention also comprises the method of making these diisocyanates described below by the phosgenation of the diamines of the general formula:

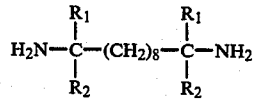

wherein $R_1$ and $R_2$ correspond to the definitions given above.

DETAILED DESCRIPTION

The diamines which are phosgenated to obtain the diisocyanates of the present invention can be obtained by hydrogenation, then hydrogenolysis of the 1,2-diaza-1,5,9-cyclododecatrienes resulting themselves from the cyclooligomerization of azines and butadiene.

The oligomerization of butadiene into cyclododecatriene is a reaction which is known and described, for instance, in U.S. Pat. No. 3,239,574, using as the catalyst titanium tetrachloride and triethylaluminum. Transition metals such as nickel can also be used as catalyst, as cited by B. BOGDANOVIC, P. HEIMBACH, M. KRÖNER, G. WILKE, E. G. HOFFMANN, and J. BRANDT in Liebigs Ann. Chem. 727, 143 (1969).

More recently some publications have shown that the introduction of nitrogen atoms into the ring was possible; French Pat. Nos. 2,189,408 and 2,292,698 and P. HEIMBACH and coworkers in Angew. Chem. Int. Ed. Engl. vol. 15, No. 1, p. 49, (1976) describe the cyclooligomerization of two molecules of butadiene with one molecule of azine in order to form 1,2-diaza-1,5,9-cyclododecatrienes.

The cyclooligomerization, in the presence of a catalyst, of azines and butadiene leading to 1,2-diaza-1,5,9-cyclododecatrienes can be written:

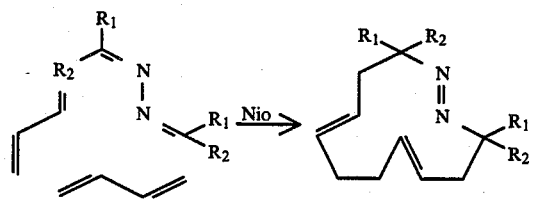

with $R_1$ and $R_2$ always corresponding to the previously given definitions.

This reaction is carried out in an inert medium in a preferably aromatic solvent such as benzene or toluene; the catalyst being prepared in situ in the solvent by the reduction of nickel-bis(acetylacetonate) with diethylethoxyaluminum, possibly in the presence of a phosphine ligand.

The hydrogenation and then hydrogenolysis of the diamine ring is usually carried out under hydrogen pressure in an organic solvent, in the presence of a catalyst. Depending on the compound, it may be necessary to operate in one or two states by possibly changing the catalyst. The >C=C< double bonds hydrogenate easily at moderate temperature, between 30° and 45° C. The hydrogenation of the N=N bond and then the opening require more severe operating conditions with temperatures above 140° C. and hydrogen pressures above 120 bars. The reaction can be schematized in the following manner:

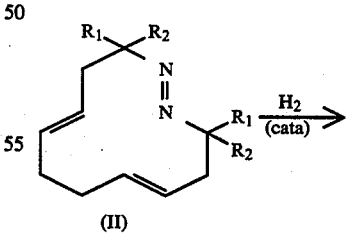

(II)

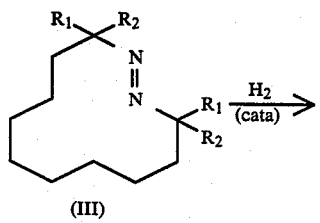

(III)

-continued

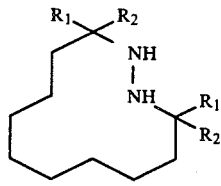

(IV)

(cata) ↓ H₂

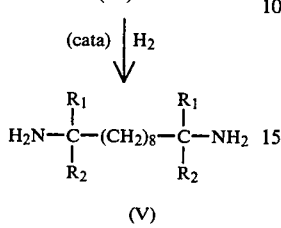

(V)

The intermediate (III) is not isolated; as for (IV), this depends on the nature of the substituents R₁ and R₂. If R₂ is different from H, it is generally preferable to operate in two stages as stated above.

The hydrogenations of the 1,2-diaza-1,5,9-cyclododecatrienes and the hydrogenolyses of the

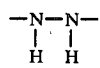

bonds are carried out in known manner, in the autoclave, in the presence of mass catalysts such as Raney nickel or supported catalysts such as palladium or rhodium deposited on charcoal or alumina. Depending on the nature of the substituents, it is preferable to adapt the hydrogenation technique. Thus, in cases in which the condensation takes place with the help of an azine derived from an aldehyde, one can operate the different states of hydrogenation with good yields in the presence of a single catalyst, such as supported rhodium, in a solvent such as tert. butanol. It is preferable to respect several temperature levels; one thus hydrogenates the double >C=C< bonds of the ring in several minutes between 30° and 40° C. under a hydrogen pressure between 100 and 120 bars, then one gradually raises the temperature to 140°–170° C. under a pressure of 140 to 200 bars for several hours in order to obtain the diamines corresponding to formula (V) given above, with R₂ being hydrogen. In case one uses a ketone as raw material, it is recommended to operate in two stages: in the first phase one hydrogenates the double >C=C< bonds of the ring, for instance in the presence of palladium deposited on charcoal, at 30°–40° C. under a pressure of 120 to 140 bars, and then in the vicinity of 100° C. under a pressure of 160 to 200 bars for several hours one converts the double —N=N bond into the

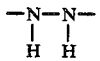

bond.

After having isolated the cyclic hydrazine thus obtained from the medium, it is again loaded into the reactor in the presence of ammonia and of another metallic catalyst such as Raney nickel. By operating in the vicinity of 200° C. under a hydrogen pressure of 120 to 140 bars for several hours, one obtains the expected diamines.

The azines corresponding to the invention are generally obtained by the reaction of one mole of hydrazine with two moles of aldehyde or of ketone according to the reaction:

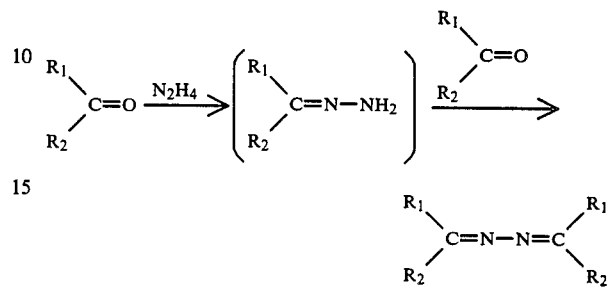

The intermediate hydrazone generally cannot be isolated.

In the case in which the reaction occurs starting with aldehyde, operation can take place according to the method described by A. N. KOST and I. I. GRANDBERT in the Journal of General Chemistry (USSR) (1955), 25, 2017; (1956), 26, 1925, 2201 and 2905 and (1961), 31, 869. At a temperature below −10° C., one pours hydrazine hydrate in slight excess on the aldehyde in solution in ether. One allows the mixture to return to ordinary temperature and potassium hydroxide in pellet form is added to saturation. The two layers are separated, the ether phase is recovered, and the azine is then distilled. In the case of ketones, the latter are added to the hydrazine hydrate at a temperature below 20° C. The water is distilled azeotropically after benzene has been readded according to the method described by T. CURTIUS and K. KHUN in the J. Prakt. Chem. (1891), 44, 92, 151, 543. Drying is finished by adding potassium hydroxide and then the organic phase is recovered and distilled.

The cyclooligomerization of the azines and butadiene can be catalyzed between 50° and 95° C. by "nude nickel" prepared in situ, that is to say nickel with zero degree of oxidation obtained by the reduction of a nickel II complex, such as nickel acetylacetonate, with an organoaluminum compound like diethylethoxyaluminum in the presence of butadiene. Customarily the molar ratio of nickel/azine can vary between 0.1 and 50% and preferably between 1 and 10%.

It is possible to operate the reduction in the presence of a ligand such as a phosphine or a phosphite capable of coordinating themselves on the metal. It is known, in fact, that in homogeneous catalysis the modification of the electronic or steric parameters of the ligand associated with the metal is of a nature so as to orient the reaction towards different reaction processes. Various aliphatic or aromatic ligands can be used, such as trimethylphosphine, tricyclohexylphosphine, triphenylphosphine, tributylphosphine, triphenylphosphite, trimethylphosphite, and the like. The molar ratio of ligand/Ni can vary between 0.1 and 10.

An important factor in the orientation of the reaction is the ratio of butadiene to azine used. It is possible to work with the stoichiometrical quantity of butadiene in relation to the azine, but it is preferable to operate in the presence of an excess of butadiene. However, the excess must not be too great, in order to limit the formation of byproducts such as vinylcyclohexene, cyclooctadiene and cyclododecatriene which are customarily obtained in the cyclooligomerization of butadiene. In certain cases, the derivative 1,2,5,6-tetraaza-1,5,9-cyclododecatriene can likewise be formed, resulting from the condensation of one mole of buadiene and two moles of azine.

The phosgenation of the diamines previously described makes it possible to obtain the isocyanates of the invention. Without being exclusive, the two techniques described below give excellent results.

According to the first technique, the diamine can be introduced into the solvent containing the dissolved phosgene and kept at a temperature below 20° C. and preferably between 0° and 20° C. A precipitate of carbamoyl chloride forms immediately. The temperature is then raised by respecting preferably, but not necessarily, a temperature level close to 60° and 100° C. From 60° C. on, one observes a solubilization of the precipitate. One terminates by refluxing of the mixture, under inert atmosphere for about three hours, then cools the mixture, filters it in order to eliminate the chlorhydrate formed, and distills the solvent as well as the diisocyanate. In this case, one can use aliphatic solvents such as decane, decaline, or aromatic solvents such as monochlorobenzene, dichlorobenzenes, and the like.

According to the second technique, in a first phase the diamine chlorhydrate is synthesized, isolated, and dried. The chlorhydrate is then placed in suspension in a solvent such as orthodichlorobenzene or tetraline and raised to refluxing temperature, close to 180°–185° C. in the case of the two solvents cited. A current of phosgene is then introduced until the precipitate is completely dissolved. One filters, distills the solvent and then the diisocyanate.

The structures of the purified products formed during the course of the different states were analyzed by nuclear magnetic resonance of the $^1H$ and $^{13}C$ atom. The current analyses were carried out by gas chromatography by using a 2-meter column filled with silicone phase SE 30 or, for the amines, a 2-meter glass column filled with chromosorb support W.N.A.W. 60-80 mesh (Johns Manville), impregnated at 5% of KOH and 5% of APIEZON N(Apiezon Products Limited) and operating isothermally at 220° C. When necessary, the identifications of the peaks were made by coupling with mass spectrometry.

The invention will be further described in connection with the following examples which are set forth for purposes of illustration only.

EXAMPLE 1

300 g of acetaldehyde in 125 ml of ether are placed into a reactor of 2-liter capacity cooled to −20° C. 136 g of hydrazine hydrate are poured in dropwise while maintaining the temperature in the vicinity of −15° C. The temperature is then allowed to return to 25° C. and then 140 g of potassium hydroxide in pellet form are added. Settling followed by decantation then takes place and the ether phase is extracted, dried, and distilled. One obtains 131 g of acetaldazine distilling at 98° C.

9.7 g of dehydrated nickel acetylacetonate (0.038 mole) and 9.8 g of triphenylphosphine (0.038 mole) solubilized in 180 ml of anhydrous benzene are introduced into a reactor of 2-liter capacity. The mixture is placed under argon and cooled to below 10° C. 9.9 g of diethyl-ethoxy aluminum (0.076 mole) are then injected.

The solution turns from a green to a maroon color and is allowed to return to ambient temperature. Then one introduces, always under argon, a mixture of 63 g of acetaldazine (0.75 mole) and 202 g of butadiene (3.7 moles) rendered soluble in 750 ml of anhydrous benzene. One insulates the reactor and brings it to 50° C. during 12 hours. The solvent is then evaporated and then the catalyst is precipitated with the aid of hexane. After filtration, one distills the mixture under 1,333 Pa and recovers 63.2 g of 3,12-dimethyl-1,2-diaza-1,5,9 cyclodecatriene distilling between 108° and 110° C. (yield 44%).

Into a stainless steel autoclave of 300 ml capacity one introduces 15 g of the condensation cycle in 105 ml of tert. butanol and one adds 1.5 g of rhodium catalyst at a concentration of 5% on alumina (ENGELHARD). After flushing the reactor with nitrogen, one introduces 120 bars of hydrogen and heats to 40° C. Reaction is allowed to take place for 30 minutes. The temperature is then allowed to go to 145° C. under 135 bars, by respecting temperature levels at 75° and 100° C. Reaction is allowed to take place for 20 hours at 145° C. followed by cooling, filtration, and distillation. One recovers 13 g of 1,10-diamino-1,10-dimethyl decane (yield: 83%) which one dissolves in 11 ml of methanol. 12.2 ml of 37% HCl are added dropwise, while limiting the temperature to 30° C. One finishes precipitating the chlorhydrate by slowly adding 140 ml of acetone. The precipitate (16.5 g) is recovered and dried. The latter is then introduced into a reactor of 100 ml capacity containing 70 ml of tetraline dried on sodium sulfate. Agitation takes place and the medium is placed under nitrogen and heated. At 150° C. a current of 1 l/h of phosgene is made to pass. At 175° C. the medium homogenizes and takes on a beige coloration which turns maroon at 180° C. One remains at the temperature plateau for one hour under flushing of phosgene until the medium becomes completely clear, then one makes a nitrogen current pass and cools the medium. The tetraline is distilled, then the isocyanate (146° C. under 400 Pa); one collects 12.35 g of colorless liquid corresponding to the 1,10-dimethyl decane-1,10-diisocyanate (NCO content of 2 equivalents per mole). Yield: 81% in relation to the chlorhydrate.

Elementary analysis: theoretical—C:66.63%—H:9.58%—N:11.10%; found:—C:66.52%—H:9.73%—N:10.86%

N.M.R. characteristics $^{13}C$ atom (chemical shifts in ppm in relation to the solvent CDCl$_3$ at 77 ppm):

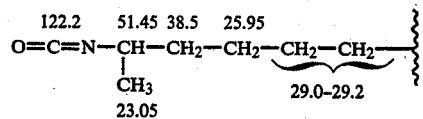

EXAMPLE 2

Isobutgraldazine is prepared by causing isobutyraldehyde to react with hydrazine hydrate according to the operating conditions described in Example 1. One then carries out the cyclooligomerization reaction of the azine with the butadiene by using a molar ratio of ½ and by operating as in Example 1 (1 at. g of Ni for 20 moles of azine). In 100 ml of tert. butanol, 14 g of 3,12-diisopropyl-1,2-diaza-1,5,9 cyclododecatriene are hydrogenated in a 300-ml autoclave, in the presence of 1.4 g of rhodium catalyst deposited at 5% on alumina. The reaction is allowed to take place for 30 minutes under 100 bars of hydrogen at 30° C., then one maintains a temperature level of 160° C. under 200 bars of hydrogen for 25 hours. 12 g of the 1,10-diamino-1,10-diisopropyl decane thus obtained are chlorhydrated and phosgenated in the same manner as in Example 1. One recovers 13.2 g of 1,10-diisopropyl-1,10-diisocyanate (phosgenation yield: 92% with respect to the amine) having an NCO group content of 1.85 equivalents per mole and presenting the following N.M.R. characteristics of the $^{13}C$ atom (chemical shifts expressed in relation to $CDCl_3$ at 77 ppm):

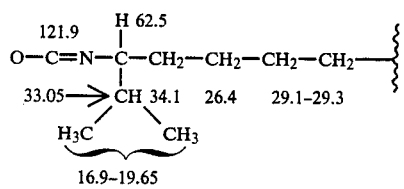

EXAMPLE 3

Propionaldazine is synthesized by the reaction of propionaldehyde with hydrazine hydrate by operating as in Example 1. The cyclooligomerization reaction is then carried out according to the conditions described in Example 1, by causing the azine to react with the butadiene in a ratio of ⅓ in the presence of nickel prepared by the reduction of nickel acetylacetonate (1 at.g. of Ni for 20 moles of azine) and of triphenylphosphine. In 100 ml of tert. butanol, 12.15 g of 3,12-diethyl-1,2-diaza-1,5,9-cyclododecatriene are hydrogenated in 300-ml autoclave, in the presence of 1.3 g of rhodium catalyst deposited at 5% on alumina. The reaction is allowed to proceed for 30 minutes at 45° C. under 130 bars of hydrogen, then for 11½ hours at 185° C. under 150 bars. The diamine (8.71 g) is phosgenated, in the form of the chlorhydrate, as in Example 1 in order to lead to 9.6 g (yield 90%) of crude isocyanate. The distillation of the latter leads to 1,10-diethyldecane-1,10-diisocyanate, a colorless liquid having a content of 2 NCO groups per mole and the following N.M.R. characteristics of the $^{13}C$ atom (chemical shifts in relation to $CDCl_3$ at 77 ppm):

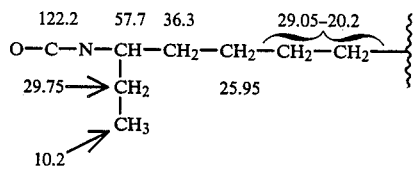

Elementary analysis: theoretical: C=70.09%; H=10.45%; N=9.08%; found: C=69.78%; H=10.25%; N=9.40%.

EXAMPLE 4

Hexahydrobenzaldazine is prepared by reaction of hexahydrobenzaldehyde with hydrazine hydrate according to the operating method described in Example 1. The 3,12-dicyclohexyl-1,2-diaza-1,5,9-cyclododecatriene is then synthesized by causing the hexahydrobenzaldazine to react with the butadiene in a molar ratio of ⅓ in the presence of nickel and of triphenylphosphine according to the description presented in Example 1 (1 at.g. of Ni for 20 moles of azine). One obtains a solid white product 10 g of which are hydrogenated in a 300-ml autoclave in 100 ml of tert. butanol in the presence of 1 g of rhodium catalyst deposited at 5% on alumina. One operates in two phases, first at 40° C. for 30 minutes under 150 bars of hydrogen, then at 216° C. for 2 hours under 157 bars. The diamine, a colorless liquid, is chlorhydrated (9.4 g) then phosgenated according to the process used in Example 1. One recovers 8.6 g of diisocyanate, of oily appearance, having an NCO content of 1.95 equivalents/mole (purity 97.5%) and presenting the following N.M.R. characteristics of the $^{13}C$ atom (chemical shifts in relation to $CDCl_3$ at 77 ppm):

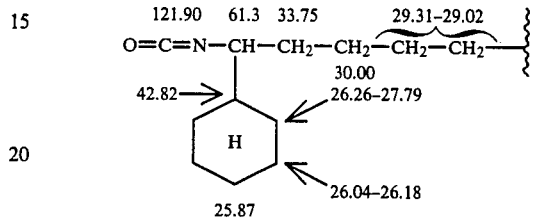

Elementary analysis: theoretical: C=74.18%; H=10.37%; N=7.21% found: C=74.07%; H=10.59%; N=7.06%

EXAMPLE 5

190 g of acetone (3.3 moles) are run dropwise on 100 g of hydrazine hydrate (2 moles), while maintaining the temperature below 17° C. The temperature is allowed to rise to 25° C. at the end of the addition, then one adds 100 ml of anhydrous benzene and eliminates the water from the reaction medium by a azeotropic distillation. One finishes drying the mixture by adding 20 g of potassium hydroxide in pellet form, separates the two layers, recovers the organic phase and distills at atmospheric pressure. One recovers 146 g of acetazine distilling at 129°-131° C.

76 g. of acetazine (0.678 moles) are made to react with 108 g of butadiene (2 moles) in the presence of nickel and of triphenylphosphine, by operating in the same manner as in Example 1. One recovers 60.5 g of 3,3,12,12-tetramethyl-1,2-diaza-1,5,9-cyclododecatriene distilling at 100° C. under 400 Pa. 20 g of this are introduced into a 300-ml autoclave containing 110 ml of ethylene glycol monoethylether and 0.9 g of palladium deposited at 5% on charcoal (ENGELHARD). One introduced 136 bars of hydrogen and the reaction is allowed to take place at 30° C. during 30 minutes, then the temperature is raised to 100° C. under 180 bars of hydrogen during 8½ hour. After cooling, expansion is allowed to take place, the reactor is emptied and filtration takes place at 40° C. One recovers 18.5 g of the corresponding cyclic hydrazine which precipitates. 10 g of this are dissolved in 60 ml of tert. butanol, and the solution is introduced into the autoclave with 5 g of freshly prepared Raney nickel and 13 g of $NH_3$. By progressively raising the temperature to 200° C., reaction is allowed to take place for 16 hours under 120 bars of hydrogen. After cooling, one filters and evaporates the solvent, then one renders the distillation residue soluble in 50 ml of orthodichlorobenzene and introduces the solution into a reactor at 10° C. containing 40 ml of phosgene dissolved in 50 ml of orthodichlorobenzene. The reaction mixture takes on a yellow coloration. One heats to 140° C. with a temperature plateau of one hour after having repeated two temperature levels; one at 60° C., the other at 100° C. The initial yellow coloration turns to maroon. After flushing with nitrogen and cooling, one filters, recovers the filtrate, and evaporates the solvent, then distills the diisocyanate (147°-150° C. under 266 Pa). One collects 2 g of 1,1,10,10-tetramethyldecane-1,10-diisocyanate (NCO content: 1.9 equivalents per mole).

Elementary analysis: theoretical: C=68.53%; H=10.06%; N=9.99% found: C=69.71%; H=10.47%; N=9.75%

N.M.R. characteristics of the $^{13}$C atom (CDCl$_3$):

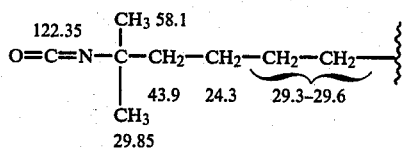

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. Decane-1,10-diisocyanates corresponding to the formula

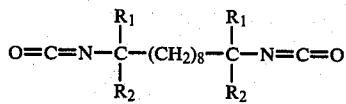

wherein R$_1$ is an alkyl or cycloalkyl radical and R$_2$ is a hydrogen atom or an alkyl or cycloalkyl radical.

2. Diisocyanates according to claim 1, wherein the alkyl radicals are radicals with a straight or branched chain having from 1 to 10 carbon atoms.

3. Diisocyanates according to claim 2, wherein the branched chains of the branched alkyl radicals are alkyl groups.

4. Diisocyanates according to claim 1, wherein the cycloalkyl radicals have from 5 to 10 carbon atoms.

5. The method of making the diisocyanates of claims 1, 2, 3, or 4 comprising phosgenating a 1,10-diamino decane of the formula

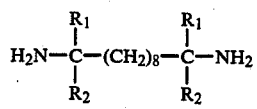

wherein R$_1$ and R$_2$ represent the hydrogen or the radicals as defined in claims 1, 2, 3, or 4.

6. The method of claim 5, wherein the diamine is placed in contact with the phosgene in a solvent medium at a temperature below 20° C. and then phosgenating at the refluxing temperature of the mixture.

7. The method of claim 5, wherein the diamine is first converted into the corresponding chlorhydrate, which chlorhydrate is reacted with the phosgene in a solvent medium at the refluxing temperature of the mixture.

8. The method of claims 5, 6, or 7, wherein the 1,10-diamino decane is obtained by hydrogenation then hydrogenolysis of 1,2-diaza-1,5,9-cyclododecadiene.

9. The method of claims 5, 6, or 7, wherein 1,10-diamino decanes are obtained by hydrogenation, and then hydrogenolysis of 1,2-diaza-1,5,9-cyclododecadiene and said 1,2-diaza-1,5,9-cyclododecadiene is made by the cyclooligomerization of azine and butadiene.

* * * * *